United States Patent [19]

Mendizabal et al.

[11] Patent Number: 4,749,377

[45] Date of Patent: Jun. 7, 1988

[54] EARDRUM PRESSURE EQUALIZER

[76] Inventors: Federico M. Mendizabal, C/Negubide 7, Las Arenas (Vizcaya); Esteban S. Basaguren, C/Maria de Molina 12, Madrid, both of Spain

[21] Appl. No.: 860,496

[22] Filed: May 7, 1986

[30] Foreign Application Priority Data

May 8, 1985 [ES] Spain .................................. 296592
Apr. 23, 1986 [ES] Spain .................................. 293768

[51] Int. Cl.$^4$ ...................... A61M 13/00; A61F 11/00
[52] U.S. Cl. ...................................................... 604/28
[58] Field of Search .......................... 604/26, 151, 152

[56] References Cited

U.S. PATENT DOCUMENTS

| | | | |
|---|---|---|---|
| 2,059,500 | 11/1936 | Thomas | 604/26 |
| 2,458,959 | 1/1949 | Reynolds | 604/26 X |
| 2,539,189 | 1/1951 | Garrett | 604/26 X |
| 4,207,887 | 6/1980 | Hiltebrandt et al. | 604/26 |
| 4,464,169 | 8/1984 | Seam | 604/26 |

Primary Examiner—Edward M. Coven
Attorney, Agent, or Firm—Henry Sternberg; Bert J. Lewen

[57] ABSTRACT

An eardrum pressure equalizer for the treatment of middle ear impairment having a source of compressed air for supplying dry room temperature air at a pressure of an order of magnitude of aproximately 3.5 kgs. per square centimeter. The air is supplied to a storage tank and from there, by way of a second storage receptacle to a disposable applicator tip adapted to be inserted into a nasal passage. The apparatus includes electronic circuitry having a microprocessor for accurately controlling the pressure of the air in the storage tank and for permitting the apparatus to be selectively used in either a continuous flow or an interrupted flow mode while allowing the pressure to be maintained at any chosen value, with a resolution factor of approximately 1/10 kg. per square centimeter.

8 Claims, 3 Drawing Sheets

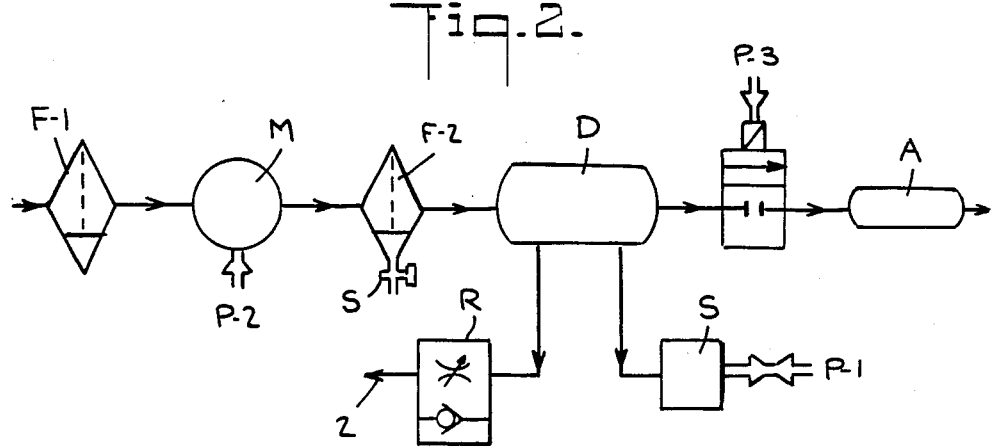
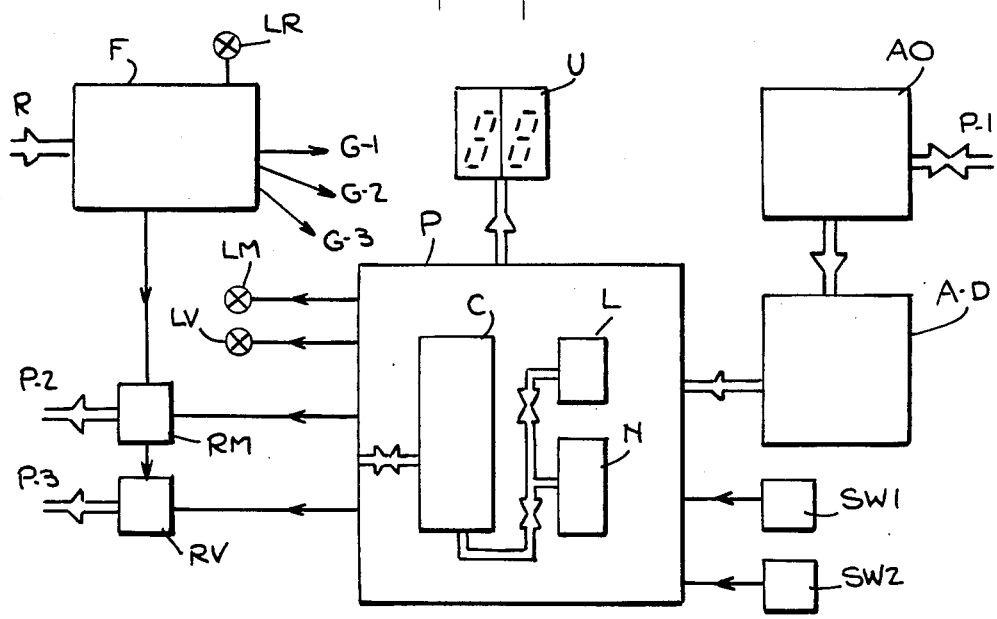

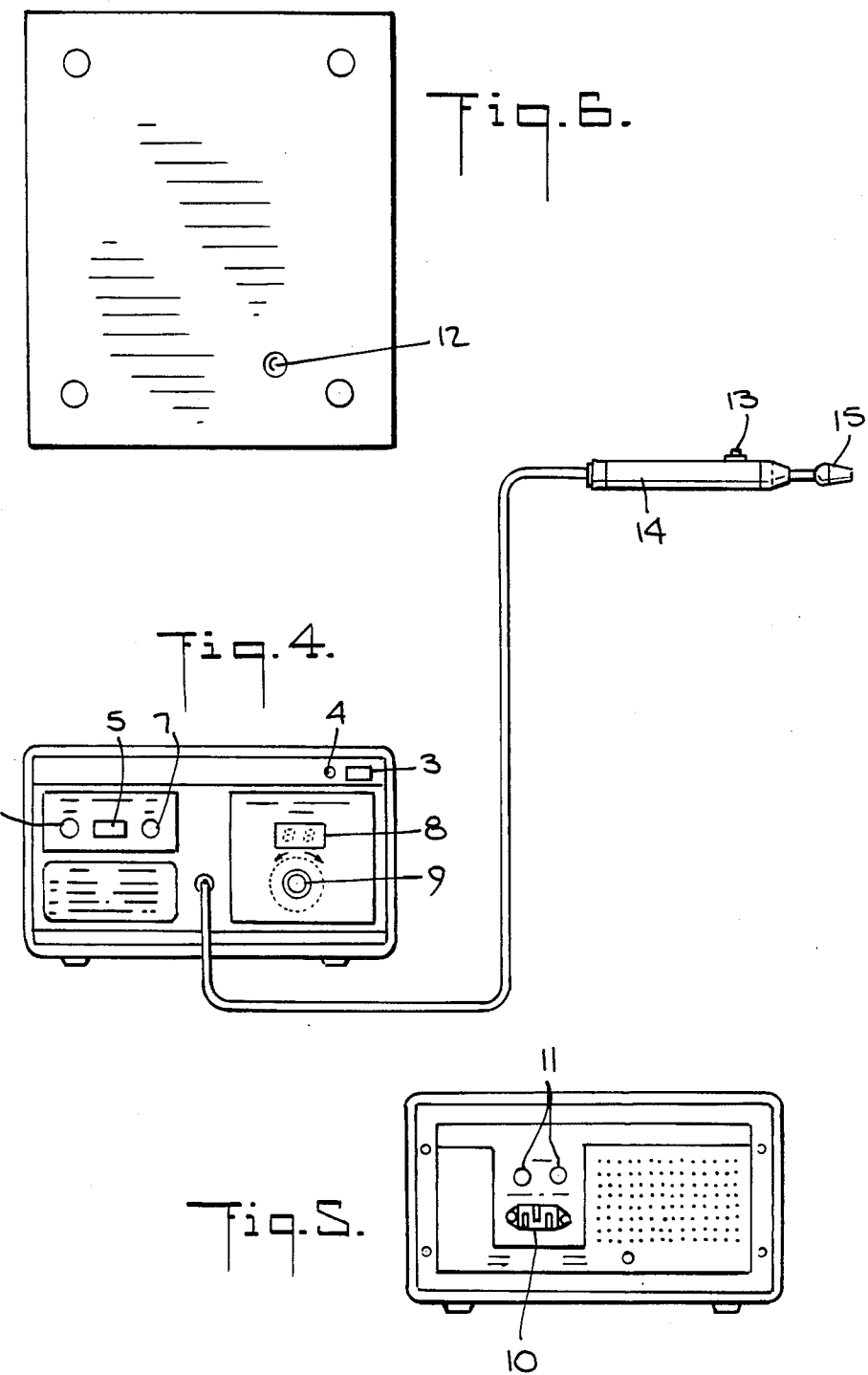

EARDRUM PRESSURE EQUALIZER

BACKGROUND OF THE INVENTION

The present invention relates to an eardrum pressure equalizer intended for the treatment of (middle ear) sound-transmission hypacusia (hearing impairment).

Hitherto, this treatment has been performed by means of a Politzer bulb or bag, invented last century by the Viennese ear-and-nose specialist of the same name. With this device one tried to attain the appropriate pressure, basically through the eustachian tube, in the tympanic cavity.

This device is based on the use of a bulb by the compression of which one achieves the supply of air at a given pressure, depending on the force with which the bulb is squeezed. As a result, the said device is attended by the drawback of providing discontinuous, low and uncontrollable, as well as unmeasurable pressures, since they are a function of the manual action. As a result it is practically impossible to introduce continuously appropriate medication into the eustachian tube.

It is the object of the present invention to obtain a device of simple design, operation, and handling so that it can be used by the ear-and-nose specialist or by the patient himself. At the same time, the device of the invention is of relatively low cost, and its operation is fast and efficient.

By means of the pressure equalizer of the invention one obtains the supply of a constant pressure, measurable at any time, and that allows for the supply or furnishing of the appropriate medication at any time.

According to the present invention, the pressure equalizer comprises a low-power air compressor, driven by means of an electric motor, a tubular compressed-air storage device connected to the compressor, and a nozzle outlet connected to the storage device.

The compressor, besides being of low power, is not to operate with oil so as to prevent iatrogenic problems (not to introduce oil particles into the ear).

Another object of the present invention is to obtain a pressure equalizer equipped with auxiliary elements, which include a microprocessor, that make it possible to increase the applications, to facilitate the applied treatment, and to simplify its handling.

SUMMARY OF THE INVENTION

The pressure equalizer of the invention includes, at the air inlet to the compressor, a particle filter and, at the outlet of said compressor, another filter of the dry type, for the removal of solid and liquid particles.

The motor-compressor is of the type of those supplied with electric power from the domestic line and is to be of the membrane type for the purpose of removing the possible presence of oil that may be harmful to be persons treated. On the other hand, the membrane compressors are apt to be of low pressure (maximum 3.5 kg/sq cm), which results in a lesser risk for the patients and the user in the event of breakdown of the pressure-control means.

The filter at the compressor outlet has a drainage valve to remove the water accumulated in the filter during filtering, which is accessible from the outside of the device in order to remove the liquid in this manner.

Through the dry filter, air is introduced into an appropriately arranged tank whose internal pressure is rising concomitantly with the operation of the motor-compressor.

In the air tank there are provided three air connections or outlets;

(a) a first one leads to a pressure sensor or pressure transducer that converts the pressure measurement into an electrical measurement;

(b) a second one, settable from outside the device, leads to a variable pressure regulator which, according to the position it is in, will keep the pressure in the tank the same by allowing for the removal of excess air so as to keep the pressure constant, by means of a discharge valve.

(c) a third connection that constitutes the outlet of air for its use in the medical treatment and is provided with an electrically operated valve, i.e., a solenoid valve. This valve will allow the release of air from the tank. The outflow will be continuous if it is kept permanently open and will be momentary if it is opened for a brief period of time. The two modes of operation of the pressure equalizer are controlled by the actuating of this valve.

The air outlet of the tank is connected from the control panel of the device or the front portion of the same to the applicator that is made up of a small tank or storage device with which it performs the two functions of pressure applicator and regulator. At the opposite end of the air-hose connection there is a constriction on which there is mounted the disposable olive-shaped tip for direct application on the patient. On the body of the applicator there is arranged a pushbutton which, upon being actuated, causes the opening of the discharge valve in the momentary discharge operating mode.

For an accurate control of the operation of the device, there has been provided a microprocessor as a most modern and reliable electronic means that performs the control functions, assisted by complementary circuitry, as described below:

(1) it interprets a signal generated by the pressure transducer and converts it into a measurement of the pressure in the tank, by showing the value thereof with at least two digits on the front panel by means of numerical indicators of LED, liquid crystal diodes, or similar diodes. The resolution is in this case of 0.1 kg/sq cm although the accuracy is much higher. Analog-digital conversion means are used that confirm the high accuracy obtained;

(2) the microprocessor receives one of the two operating orders in one of the two discharge modes: continuous or momentary These two orders are given on the front panel of the device. Upon choosing the operation as continuous discharge, the microprocessor acts by turning on an indicator light of the mode of operation, opens the electrically operated discharge valve by letting out the air freely, and shows the pressure present in the tank. Upon choosing the momentary discharge operation, it turns on the corresponding indicator light, keeps the electrically operated valve closed, shows the pressure in the tank and will let the air out momentarily only when the discharge pushbutton located on the applicator is pressed. The order coming from the pushbutton is of circuit closing, and goes to one of the order inputs of the microprocessor. Upon pressing the contents of the pushbutton, the tank are discharged onto the patient for as long as the pushbutton is depressed;

(3) when the device is connected to the line, the microprocessor initiates the start-up process by opening the electrically operated valve and discharging the tank

["contents"-Translator] in the event that a pressure exists therein, up to a given level, actuates the motor as soon as the pressure has come down from said level and then closes the electrically operated valve, the device being normally ready for its use within a time estimated as 6 seconds as a maximum.

BRIEF DESCRIPTION OF THE DRAWINGS

As a nonlimitative exemplified embodiment, the annexed drawings describe and schematically illustrate a Preferred Embodiment which will help give a better understanding of the invention and in which:

FIG. 3 represents a block diagram of the electronic control circuit of the device constituted according to FIG. 2;

FIGS. 4, 5, and 6, a practical embodiment is represented in front elevation, rear elevation, and bottom plan;

FIG. 7 represents in plan view the layout of the various components inside the housing of the device.

DESCRIPTION OF THE PREFERRED EMBODIMENT

Figure 1:
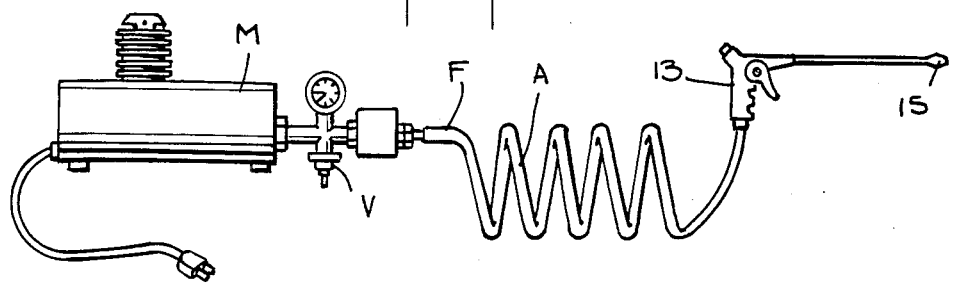
FIG. 1 represents, schematically, one possible mode of a simplified embodiment.

As can be seen in FIG. 1, the pressure equalizer comprises a low-power compressor M driven by means of an electric motor that can be connected to the line by means of the corresponding cord and plug. At the outlet of the compressor M there is provided a pressure gauge, indicator of the supplied air pressure, as well as a hand-adjusted pressure reducer or decompression valve V. The device is likewise provided with a filter for the retention of possible particles that may be carried along by the air supplied by the compressor M. At the outlet of the filter F there is connected a flexible and sturdy hose A at the free end of which there is connected a shutoff valve 13 shaped, for instance, in the form a hand-operted pistol. To the outlet of the valve there is connected a flexible tube terminated by an outlet nozzle 15 for the application of the treatment.

The tube is to be of sufficient length to allow the necessary mobility of the nozzle and the pistol and to serve, at the same time, as a compressed-air storage device that will permit compressed air to be available at any time for its supply through the nozzle continuously or in bursts.

In the circuit between the compressor and the pistol there can be provided a chamber that contains the medication to be applied.

Figure 2:
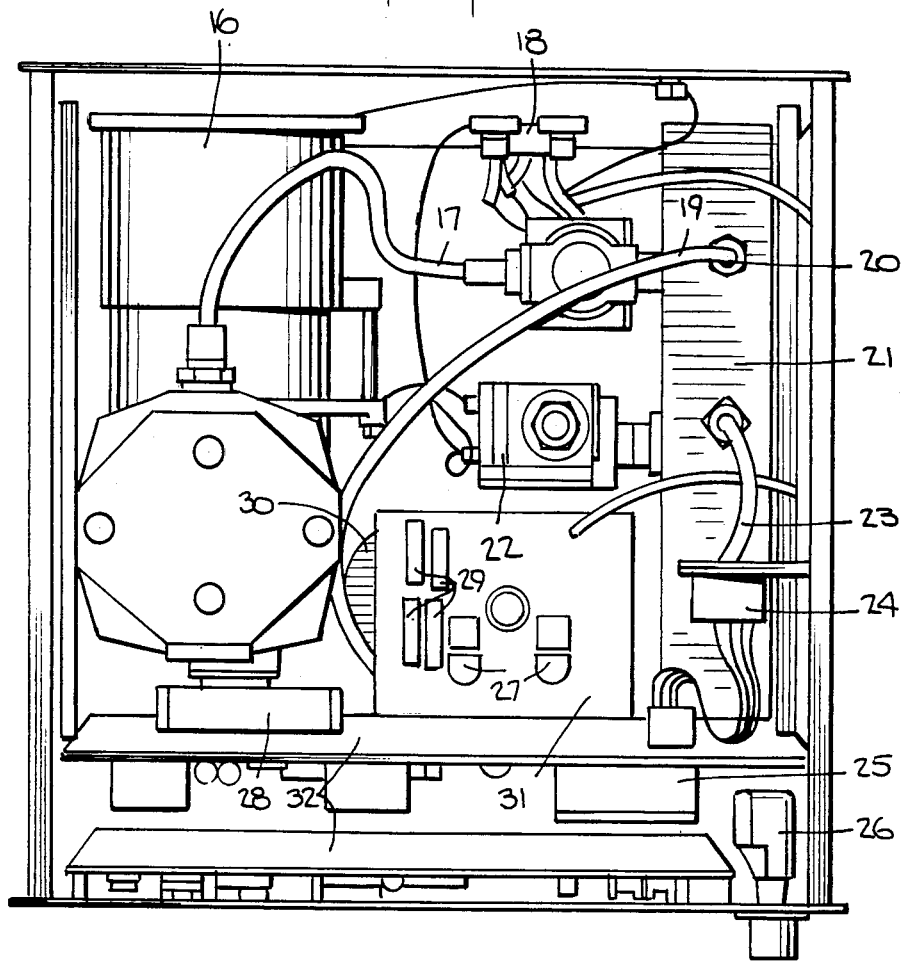
FIG. 2 shows a pneumatic diagram of a device according to one embodiment of the invention.

FIG. 2 represents a pneumatic diagram of the device. The motor compressor M operates when electric power is supplied to it through the connection P-2 from the control device with microprocessor. It receives air through the filter F-1, compresses it and passes it through the second dry filter F-2, which has a water-drainage valve S that is accessible from the outside, for the purpose of removing the water condensed therein during the operation. From the dry filter, it passes to the tank D in which air is stored at the pressure selected manually on the regulator R; the excess air is expelled automatically via the outlet 2 of the regulator so as to maintain a constant pressure in the tank.

To the tank there is connected a strain-gauge-bridge sensor or transducer S that receives exciting current from the electronic control circuits, to which it transmits likewise the transducing signal through the wires P-1. With this sensor the pressure inside the tank is measured at all times with an accuracy superior to mechanical type manometers.

At the outlet of the air tank is the discharge valve V which serves to transmit the compressed air to the air storage device A, arranged in this case in the same applicator, at whose other extremity there is provided a mouthpiece 1 that receives the olive applicator.

The discharge valve receives the activating voltage through the electric wires P-3 from the control circuits.

This valve will stay open permanently during the continuous discharge operating mode, and will stay open only during the time when a pushbutton located on the applicator is depressed, when the device is operated in the momentary discharge.

In FIG. 3 there is represented a block diagram of the electronic control circuit.

By P there is represented the microprocessor block; in it there are contained the CPU C, and EPROM memory block N, and a 'Lach' of program reading and interpreting. Orders and signals arrive at the microprocessor. It receives orders to operate in the continuous discharge or the momentary discharge mode, both coming from an ordinary transfer switch symbolized by SW1. It is given a triggering order for the continuous-discharge mode of operation by means of the closing of a pushbutton symbolized by SW2 and located on the storage device or, in this case, applicator symbolized by A in FIG. 1.

The signals it receives come from the pressure sensor or pressure voltage transducer, for that purpose one uses a strain-gauge type bridge that receives a constant current from the circuit symbolized by AO, the bridge in turn returns a voltage, a function of the said current and the pressure inside the tank, to the same circuit, which, after appropriately amplifying and stabilizing it, transmits it to an analog-digital converter that make it processable by the microprocessor. The sensor signal and the exciting current are carried through the wires symbolized by P-1 between AO and S.

The digital signal at the output of the converter AD is identified by the microprocessor that converts them into figures legible in the digital indicator U, symbolized in this case by seven-segment digits.

In its peripheral circuitry the microprocessor is provided with all the auxiliary means that are common to these devices such as: quartz crystal, impedance adaptors, and discrete components, etc.

The auxiliary means of the microprocessor and of the circuits shown as blocks, consisting of integrated circuits and discrete components of current use, are not shown because there exist multiple ways of individual realization that achieve the same results and that are commonly used in electronics.

According to the orders received and the mentioned modes of operation, the microprocessor actuates relays or devices for converting an order into a power signal [and,] as shown in FIG. 2, they actuate the motor-compressor and the electrical valve.

In the case of the motor-compressor, it will be actuated through the power circuit RM and the electric line P-2.

In the case of the electrically operated discharge valve, it will be done through the power circuit RV and the line P-3.

Depending on the actuating of the operating-mode transfer switch SW1, an indicator light LM will be turned on to signal continuous discharge or LV for momentary discharge.

All of the mentioned circuits are fed from the electrical line R by means of a power supply source F which produces the different d-c supply voltages G-1, G-2, and G-3, comprises the appropriate elements for voltage-stabilized d-c supply sources.

FIGS. 4, 5, and 6 show in front elevation, rear elevation, and bottom plan, a practical embodiment in which the various reference numerals represent: 3 the start-up switch; 4 the start-up indicator light; 5 the operating mode selector switch; 6 the momentary-discharge indicator light; 7 the continuous-discharge indicator light; 8 the digital pressure indicator; 9 the internal-pressure control and adjustment scale; 10 the line connector; 11 the protective fuses; 12 the drainage-valve opening; 13 the momentary discharge triggering button; 14 the applicator and at the same time storage device; and 15 the disposable olive-shaped tip for the applicator.

In FIG. 7 there is shown a drawing representing a plan view of the layout, inside the pressure-equalizer housing, of the different elements that constitute it: 16 the motor-compressor, 17 line from the motor-compressor to the dry filter; 18 line-voltage connection; 19 air line from the tank to the applicator; 20 dry air filter; 21 air tank; 22 electrically operated discharge valve; 23 air line from the tank to the transducer; 24 transducer; 25 pressure control knob and regulator; 26 line connection switch; 27, 28, 29, and 30 various electronic components on the printed circuit plates 31 and 32.

Having sufficiently described the nature of the invention, as well as the manner of materializing it in practice, it should be pointed out that the arrangements set forth above may be changed in detail, provided that their basic principle is not altered.

We claim:

1. An eardrum pressure equalizer apparatus for the treatment of the middle ear comprising:
   a source of compressed air at room temperature, at a pressure not in excess of 3.5 kg. per square centimeter, and said air being substantially free of oil and water;
   air storage means for storing a quantity of air at substantially constant pressure and for maintaining that pressure substantially constant even as air is being withdrawn from said storage means;
   conduit means for connecting said source of compressed air with said air storage means;
   discharge valve means for controlling the flow of air out of said air storage means;
   second conduit means connecting said air storage means with said discharge valve means;
   second air storage means downstream of said discharge valve means;
   applicator means having an upstream end and a downstream end;
   third conduit means connecting said upstream end of said applicator means with said second air storage means; and
   disposable tip means adapted to be inserted into one nostril of the patient and to be received on said downstream end of said applicator means, said applicator means having a portion of constricted flow between said upstream and said downstream end thereof for constricting the flow of air to said tip means.

2. The apparatus according to claim 1, wherein said source of compressed air comprises a membrane compressor, electric motor means operatively connected to drive said membrane compressor and filter means cooperating with said compressor for filtering the air flowing through the compressor and removing liquid therefrom.

3. The apparatus according to claim 1, comprising means for continuously sensing the pressure in said first mentioned air storage means, electronic control means including microprocessor means operatively connected with said sensing means and with said compressor means for controlling the operation of said compressor means and circuit means connecting said microprocessor means and said discharge valve means for permitting the unit to operate selectively either as an instaneous-air-discharge, or as a continuous-air discharge unit.

4. The apparatus according to claim 3 wherein said applicator means comprises push button control means for allowing manual selection between intermittent or continuous air flow operation.

5. The apparatus according to claim 3 wherein said microprocessor coopertes with said motor drive means and with said discharge valve means for regulating the air pressure and the operational mode of the apparatus.

6. The apparatus according to claim 3 further comprising electronic readout means for allowing the operator to observe the exact air pressure in the system available for use, said means comprising digital indicator means capable of distinguishing between pressures varying by 1/10 of a kg per square centimeter.

7. The apparatus according to claim 1 wherein said disposable tip means is olive-shaped.

8. Eardrum pressure equalizer comprising: low-pressure air compressor means, air storage means, fluid conduit means connecting said air storage means and said compressor means, applicator nozzle means, and second fluid conduit means connecting said air storage means with said applicator means for flow of air to said applicator means, electronic measurement means cooperative with said storage means for measuring the air pressure therein, electric valve means for controlling the air output from said storage means, air filter means cooperative with said compressor means for filtering the air from said compressor means, pressure selector means for selecting the air pressure to said applicator nozzle means, microprocessor means including electric circuit means operatively connected to said pressure selector means, said pressure selector means comprising a pressure transducer and digital indicator means for controlling said electric valve means to selectively provide continuous or instantaneous discharge of air from said applicator means and pushbutton means on said applicator means for manually controlling the air output from said applicator means.

* * * * *